US009358288B2

(12) United States Patent
Sela et al.

(10) Patent No.: US 9,358,288 B2
(45) Date of Patent: Jun. 7, 2016

(54) ANTIBODY COMBINATIONS AND USE OF SAME FOR TREATING CANCER

(71) Applicant: Yeda Research and Development Co. Ltd., Rehovot (IL)

(72) Inventors: Michael Sela, Rehovot (IL); Yosef Yarden, Rehovot (IL); Bilha Schechter, Rehovot (IL); Tsipi Ben-Kasus, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 14/536,754

(22) Filed: Nov. 10, 2014

(65) Prior Publication Data

US 2015/0056216 A1 Feb. 26, 2015

Related U.S. Application Data

(62) Division of application No. 13/063,940, filed as application No. PCT/IL2009/000816 on Aug. 19, 2009, now Pat. No. 8,883,149.

(60) Provisional application No. 61/096,868, filed on Sep. 15, 2008.

(51) Int. Cl.
*C07K 16/32* (2006.01)
*A61K 39/395* (2006.01)
*A61K 39/00* (2006.01)

(52) U.S. Cl.
CPC ............. *A61K 39/3955* (2013.01); *C07K 16/32* (2013.01); *A61K 2039/505* (2013.01); *A61K 2039/507* (2013.01); *C07K 2317/565* (2013.01)

(58) Field of Classification Search
CPC ............. C07K 16/32; C07K 2317/565; A61K 39/3955; A61K 2039/507; A61K 2039/505
USPC ...................................... 424/158.1
See application file for complete search history.

(56) References Cited

U.S. PATENT DOCUMENTS

| 5,587,458 A | 12/1996 | King et al. |
| 5,693,762 A | 12/1997 | Queen et al. |
| 7,498,142 B2 | 3/2009 | Yarden et al. |
| 2003/0086924 A1 | 5/2003 | Sliwkowski |
| 2003/0170235 A1 | 9/2003 | Cohen |
| 2007/0178102 A1 | 8/2007 | Yarden et al. |
| 2009/0155288 A1 | 6/2009 | Yarden et al. |
| 2014/0086917 A1 | 3/2014 | Sela et al. |

FOREIGN PATENT DOCUMENTS

| WO | WO 2004/032960 | 4/2004 |
| WO | WO 2007/076923 | 7/2007 |
| WO | WO 2008/031531 | 3/2008 |
| WO | WO 2010/022736 | 3/2010 |
| WO | WO 2010/029534 | 3/2010 |
| WO | WO 2011/107957 | 9/2011 |
| WO | WO 2012/059857 | 5/2012 |
| WO | WO 2012/156975 | 11/2012 |

OTHER PUBLICATIONS

NCI-N87 cell line from the ATCC (p. 1; Sep. 17, 2015).*
Maron et al. PNAS 110(38):15389-15394 (Sep. 17, 2013).*
Communication Pursuant to Article 94(3) EPC Dated Oct. 16, 2014 From the European Patent Office Re. Application No. 12726895.1.
Ex Parte Quayle Official Action Dated Mar. 25, 2014 From the US Patent and Trademark Office Re. U.S. Appl. No. 13/063,940.
International Preliminary Report on Patentability Dated Mar. 24, 2011 From the International Bureau of WIPO Re.: Application No. PCT/IL2009/000816.
International Preliminary Report on Patentability Dated Nov. 28, 2013 From the International Bureau of WIPO Re. Application No. PCT/IL2012/050176.
international Search Report and the Written Opinion Dated Feb. 15, 2010 From the International Searching Authority Re.: Application No. PCT/IL2009/000816.
International Search Report and the Written Opinion Dated Jul. 23, 2012 From the International Searching Authority Re. Application No. PCT/IL2012/050176.
Office Action Dated May 5, 2013 From the Israel Patent Office Re. Application No. 211752 and Its Translation Into English.
Official Action Dated Nov. 1, 2007 From the US Patent and Trademark Office Re.: U.S. Appl. No. 11/342,615.
Official Action Dated Apr. 5, 2013 From the US Patent and Trademark Office Re. U.S. Appl. No. 13/072,839.
Official Action Dated Sep. 6, 2013 From the US Patent and Trademark Office Re. U.S. Appl. No. 13/063,940.
Official Action Dated Sep. 6, 2013 From the US Patent and Trademark Office Re. U.S. Appl. No. 14/118,243.
Official Action Dated Sep. 7, 2012 From the US Patent and Trademark Office Re. U.S. Appl. No. 13/072,839.
Official Action Dated Nov. 9, 2010 From the US Patent and Trademark Office Re. U.S. Appl. No. 12/320,207.
Official Action Dated Apr. 10, 2012 From the US Patent and Trademark Office Re. U.S. Appl. No. 13/072,839.
Official Action Dated Apr. 11, 2007 From the US Patent and Trademark Office Re.: U.S. Appl. No. 11/342,615.
Official Action Dated Sep. 17, 2009 From the US Patent and Trademark Office Re.: U.S. Appl. No. 12/320,207.
Official Action Dated Jan. 20, 2010 From the US Patent and Trademark Office Re.: U.S. Appl. No. 12/320,207.
Official Action Dated Jul. 21, 2010 From the US Patent and Trademark Office Re.: U.S. Appl. No. 12/320,207.
Official Action Dated May 22, 2008 From the US Patent Office Re.: U.S. Appl. No. 11/342,615.

(Continued)

Primary Examiner — Lynn Bristol

(57) ABSTRACT

A method of identifying a combination of antibodies with a combined improved anti-tumor activity is provided. The method comprising: (a) identifying binding epitopes of anti ErbB-2 antibodies; and (b) selecting a combination of at least two antibodies of the anti ErbB-2 antibodies exhibiting binding to different epitopes on the ErbB-2, at least one of the different epitopes being localized to a dimerization site of the ErbB-2, the combination of antibodies being with the combined improved anti-tumor activity. Also provided are novel antibody combinations uncovered according to the present teachings.

5 Claims, 5 Drawing Sheets

(56) References Cited

OTHER PUBLICATIONS

Summons to Attend Oral Proceedings Pursuant to Rule 115(1) EPC Dated Jul. 3, 2012 From the European Patent Office Re. Application No. 09787543.9.
Arteaga "The Epidermal Growth Factor Receptor: From Mutant Oncogene in Nonhuman Cancers to Therapeutic Target in Human Neoplasia", Journal of Clinical Oncology, 19(18/Suppl.): 32s-40s, Sep. 15, 2001.
Baselga et al. "Objective Response Rate in a Phase II Multicenter Trial of Pertuzumab (P), a HER2 Dimerization Inhibiting Monoclonal Antibody, in Combination With Trastuzumab (T) in Patients (PTS) With HER2-Positive Metastatic Breast Cancer (MBC) Which Has Progressed During Treatment With T", Journal of Clinical Oncology, Clinical Science Symposium, Oral Presentation, P.33s: # 1004, 2007.
Beckman et al. "Antibody Constructs in Cancer Therapy. Protein Engineering Strategies to Improve Exposure in Solid Tumors", Cancer, 109: 170-179, 2007.
Ben-Kasus et al. "Cancer Therapeutic Antibodies Come of Age: Targeting Minimal Residual Disease", Molecular Oncology, 1: 42-54, 2007.
Ben-Kasus et al. "Persistent Elimination of ErbB-2/HER2-Overexpressing Tumors Using Combinations of Monoclonal Antibodies: Relevance of Receptor Endocytosis", Proc. Natl. Acad. Sci. USA, XP002562767, 106(9): 3294-3299, Mar. 2009.
Brand et al. "Prospect for Anti-HER2 Receptor Therapy in Breast Cancer", Anticancer Research, 26: 463-470, 2006.
Cespedes et al. "Mouse Models in Oncogenesis and Cancer Therapy", Clinical & Translational Oncology, 8(5): 318-329, May 2006.
Chen et al. "An Immunological Approach Reveals Biological Differences Between the Two NDF/Heregulin Receptors, ErbB-3 and ErbB-4", The Journal of Biological Chemistry, 271(13): 7620-7629, 1996.
Dennis "Off by a Whisker", Nature, 442: 739-741, 2006.
Drebin et al. "Monoclonal Antibodies Reactive With Distinct Domains of the Neu Oncogene-Encoded P185 Molecule Exert Synergistic Anti-Tumor Effects in Vivo", Oncogene, 2(3): 273-277, 1988.
Dugan et al. "HER-2/Neu Expression in Pancreatic Adenocarcinoma: Relation to Tumor Differentiation and Survival", Pancreas, 14(3): 229-236, 1997.
Friedman et al. "Synergistic Down-Regulation of Receptor Tyrosine Kinases by Combinations of mAbs: Implications for Cancer Immunotherapy", Proc. Natl. Acad. Sci. USA, PNAS, 102(6): 1915-1920, 2005.
Fujimori et al. "A Modeling Analysis of Monoclonal Antibody Percolation Through Tumors: A Binding-Site Barrier", Journal of Nuclear Medicine, 31: 1191-1198, 1990.
Goldstein et al. "Biological Efficacy of a Chimeric Antibody to the Epidermal Growth Factor Receptor in a Human Tumor Xenograft Model", Clinical Cancer Research, 1(11): 1311-1318, Nov. 1995.
Harwerth et al. "Monoclonal Antibodies Directed to the ErbB-2 Receptor Inhibit in Vivo Tumour Cell Growth", British Journal of Cancer, 68(6): 1140-1145, Dec. 1993.
Heitner et al. "Selection of Cell Binding and Internalizing Epidermal Growth Factor Receptor Antibodies From a Phage Display Library", Journal of Immunological Methods, 248: 17-30, 2001.
Hurwitz et al. "Suppression and Promotion of Tumor Growth by Monoclonal Antibodies to ErbB-2 Differentially Correlate With Cellular Uptake", Proc. Natl. Acad. Sci. USA, 92(8): 3353-3357, 1995.
Johns et al. "Identification of the Epitope for the Epidermal Growth Factor Receptor-Specific Monoclonal Antibody 806 Reveals That It Preferentially Recognizes an Untethered Form of the Receptor", The Journal of Biological Chemistry, 279(29): 30375-30384, Jul. 16, 2004.
Johnstone et al. "Manipulation and Storage of Immunoglobulins", Immunochemistry in Practice, Blackwell Scientific Publications, 2nd Ed.: 49-50, 1987.
Kamat et al. "Enhanced EGFR Inhibition and Distinct Epitope Recognition by EGFR Antagonistic mAbs C225 and 425", Cancer Biology & Therapy, 7(5): 726-733, May 2008.
Kasprzyk et al. "A Therapy of an Animal Model of Human Gastric Cancer Using a Combination of Anti-ErbB-2 Monoclonal Antibodies", Cancer Research, 52(10): 2771-2776, 1992.
Kipriyanov et al. "Recent Advances in the Generation of Bispecific Antibodies for Tumor Immunotherapy", Current Opinion in Drug Discovery & Development, 7(2): 233-242, 2004.
Klapper et al. "A Subclass of Tumor-Inhibitory Monoclonal Antibodies to Erb-2/HER2 Blocks Crosstalk With Growth Factor Receptors", Oncogene, XP001068241, 14(17): 2099-2109, 1997. Table 1.
Klapper et al. "Tumor-Inhibitory Antibodies to HER-2/ErbB-2 May Act by Recruiting c-Cbl and Enhancing Ubiquitination of HER-$2^{1}$", Cancer Research, 60: 3384-3388, 2000.
Larbouret et al. "Combined Cetuximab and Trastuzumab Are Superior to Gemcitabine in the Treatment of Human Pancreatic Carcinoma Xenografts", Annals of Oncology, XP002679701, 21(1): 93-103, Jan. 2010. Figs.1, 4.
Larbouret et al. "In Vivo Therapeutic Synergism of Anti-Epidermal Growth Factor Receptor and Anti-HER2 Monoclonal Antibodies Against Pancreatic Carcinomas", Clinical Cancer Research, XP009148159, 13(11): 3356-3362, Jun. 1, 2007.
Lee et al. "Monoclonal Antibody Radiopharmaceuticals: Cationization, Pegylation, Radiometal Chelation, Pharmacokinetics, and Tumor Imaging", Bioconjugate Chemistry, 14: 546-553, 2003.
Leonard et al. "Combination Antibody Therapy With Epratuzumab and Rituximab in Relapsed or Refractory Non-Hodgkin's Lymphoma", Journal of Clinical Oncology, 23(22): 5044-5051, Aug. 1, 2005.
Merimsky et al. "Induction Chemotherapy for Bone Sarcoma in Adults: Correlation of Results With ErbB-4 Expression", Oncology Reports, 10: 1593-1599, 2003.
Nahta et al. "The HER-2-Targeting Antibodies Trastuzumab and Pertuzumab Synergistically Inhibit the Survival of Breast Cancer Cells", Cancer Research, 64: 2343-2346, 2004.
Nielsen et al. "Internalizing Antibodies and Targeted Cancer Therapy: Direct Selection From Phage Display Libraries", Pharmaceutical Science & Technology Today, 3(8): 282-291, Aug. 2000.
Panousis et al. "Engineering and Characterisation of Chimeric Monoclonal Antibody 806 (CII806) for Targeted Immunotherapy of Tumours Expressing DE2-7 EGFR or Amplified EGFR", British Journal of Cancer, 92: 1069-1077, 2005.
Perera et al. "Treatment of Human Tumor Xenografts With Monoclonal Antibody 806 in Combination With a Prototypical Epidermal Growth Factor Receptor- Specific Antibody Generates Enhanced Antitumor Activity", Clinical Cancer Research, 11(17: 6390-6399, Sep. 1, 2005.
Persson et al. "[177Lu]Pertuzumab: Experimental Studies on targeting of HER-2 Positive Tumour Cells", European Journal of Nuclear Medicine and Molecular Imaging, 32(12): 1457-1462, 2005.
Rudnick et al. "Affinity and Avidity in Antibody-Based Tumor Targeting", Cancer Biotherapy and Radiopharmaceuticals, 24(2): 155-162, 2009.
Scheuer et al. "Strongly Enhanced Antitumor Activity of Trastuzumab and Pertuzumab Combination Treatment on HER2-Positive Human Xenograft Tumor Models", Cancer Research, 69: 9330-9336, 2009.
Shen et al. "In Vivo Activity of Novel Anti-ErbB2 Antibody ChA21 Alone and With Paclitaxel or Trastuzumab in Breast and Ovarian Cancer Xenograft Models", Cancer Immunology & Immunotherapy, 60: 339-348, 2011.
Slamon et al. "Studies of the HER-2/Neu Proto-Oncogene in human Breast and Ovarian Cancer", Science, 244: 707-712, May 12, 1989.
Spangler et al. "Combination Antibody Treatment Down-Regulates Epidermal Growth Factor Receptor by Inhibiting Endosomal Recycling", Proc. Natl. Acad. Sci. USA, PNAS, 107(30): 13252-13257, Jul. 27, 2010.
Spiridon et al. "A Comparison of the In Vitro and In Vivo Activities of IgG and F(ab')2 Fragments of a Mixture of Three Monoclonal Anti-Her-2 Antibodies", Clinical Cancer Research, 10: 3542-3551, 2004.

(56) References Cited

OTHER PUBLICATIONS

Spiridon et al. "Targeting Multiple Her-2 Epitopes With Monoclonal Antibodies Results in Improved Antigrowth \Activity of a Human Breast Cancer Cell Line in Vitro and in Vivo", Clinical Cancer Research, 8: 1720-1730, 2002.

Stratagene "Gene Characterization Kits", Catalog, Stratagene, p. 39, 1988.

Strome et al. "A Mechanistic Perspective of Monoclonal Antibodies in Cancer Therapy Beyond Target-Related Effects", The Oncologist, 12: 1084-1095, 2007.

Talmadge et al. "Murine Models to Evaluate Nocel and Conventional Therapeutic Strategies for Cancer", The American Journal of Pathology, 170(3): 793-804, Mar. 2007.

Thurber et al. "Antibody Tumor Penetration: Transport Opposed by Systenic and Antigen-Mediated Clearance", Advanced Drug Delivery Reviews, 60: 1421-1434, 2008.

Tokunaga et al. "Trastuzumab and Breast Cancer: Developments and Current Status", Int. J. Clin. Oncol., 11(3): 199-208, 2006, Abstract.

Troise et al. "Differential Binding of Human Immunoagents and Herceptin to the ErbB2 Receptor", The FEBS Journal, 275: 4967-4979, 2008.

Voskoglou-Nomikos et al. "Clinical Predictive Value of the in Vitro Cell Line, Human Xenograft, and Mouse Allograft Preclinical Cancer Models", Clinical Cancer Research, 9: 4227-4239, Sep. 15, 2003.

Yarden "Biology of HER2 and Its Importance in Breast Cancer", Oncology, 61(suppl 2): 1-13, 2001.

Ye et al. "Augmentation of a Humanized Anti-HER2 mAb 4D5 INduced Growth Inhibition by a Human-Mouse Chimeric Anti-EGF Receptor mAb C225", Oncogene, 18: 731-738, 1999.

Communication Pursuant to Article 94(3) EPC Dated Dec. 2, 2015 From the European Patent Office Re. Application No. 12726895.1.

Gaborit et al. "Time-Resolved Fluorescence Resonance Energy Transfer (TR-FRET) to Analyze the Disruption of EGFR/HER2 Dimers. A New Method to Evaluate the Efficiency of Targeted Therapy Using Monoclonal Antibodies", The Journal of Biological Chemistry, XP055021021, 286(13): 11337-11345, Published Online Jan. 31, 2011.

Larbouret et al. "In Vivo Therapeutic Synergism of Anti-Epidermal Growth Factor Receptor and Anti-HER2 Monoclonal Antibodies Against Pancreatic Carcinomas", Clinical Cancer Research, 13(11): 3356-3362, Jun. 1, 2007.

Shepherd et al. "The Design of the Humanized Antibody", Monoclonal Antibodies: A Practical Approach, XP008098266, Appendix 1: 58-66, Jan. 1, 2000.

\* cited by examiner

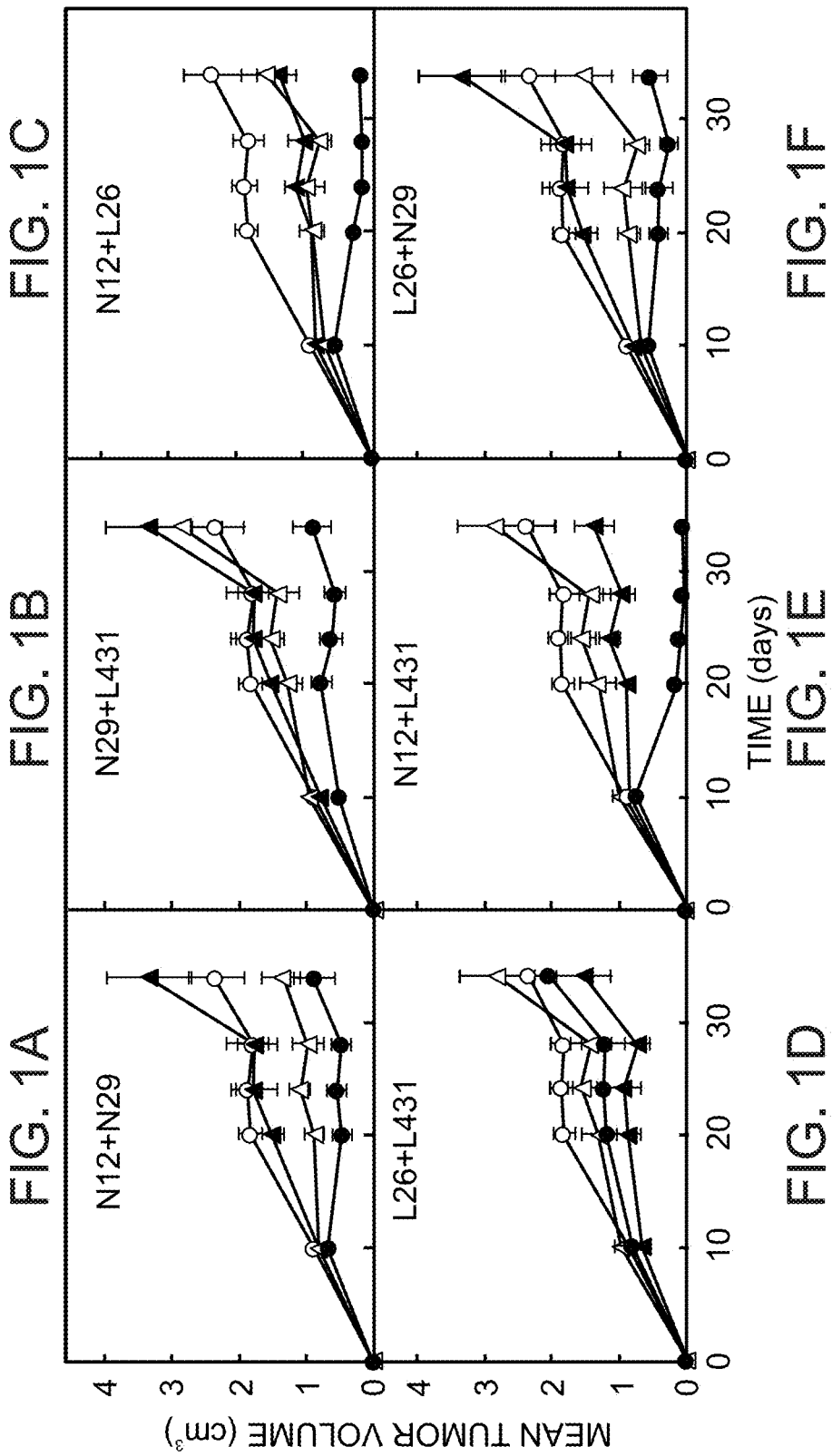

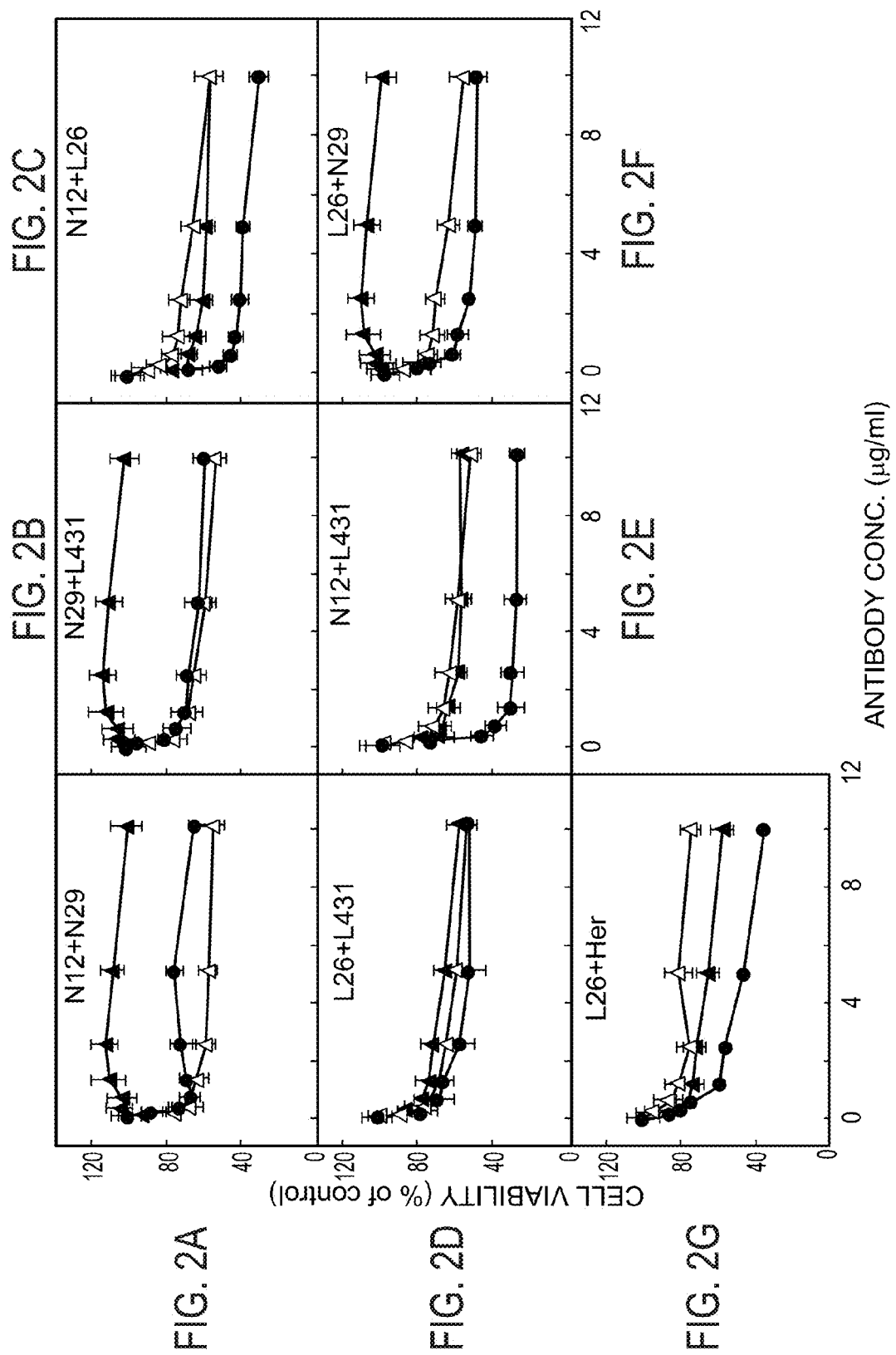

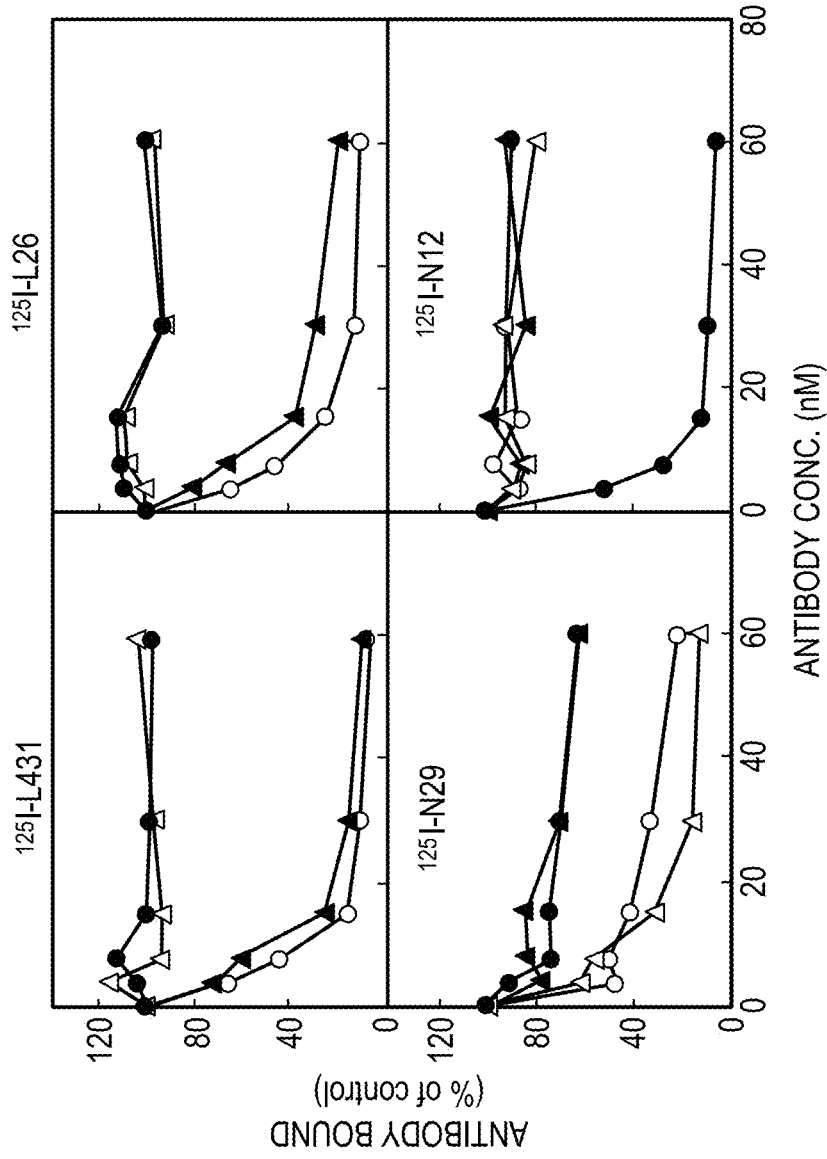

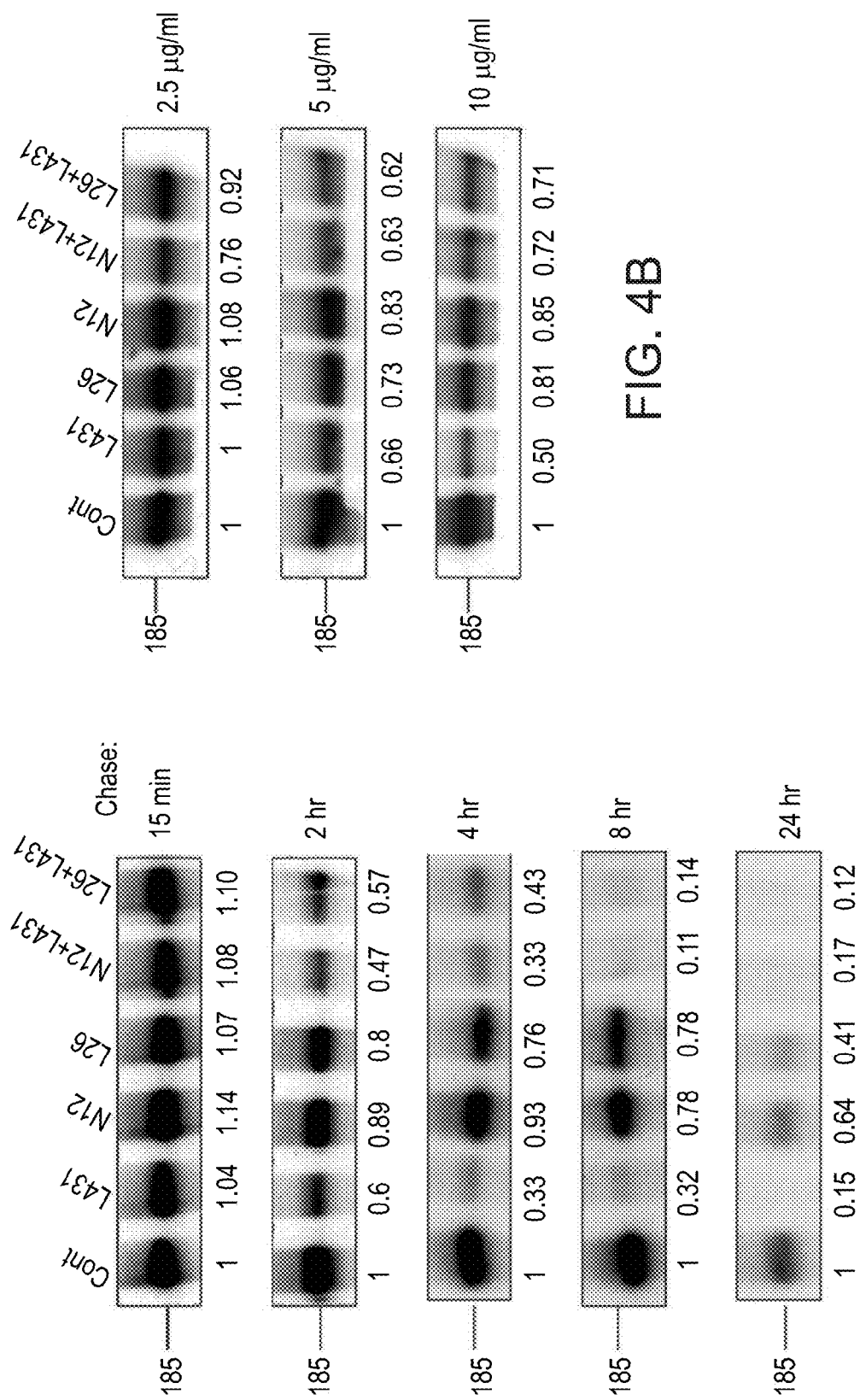

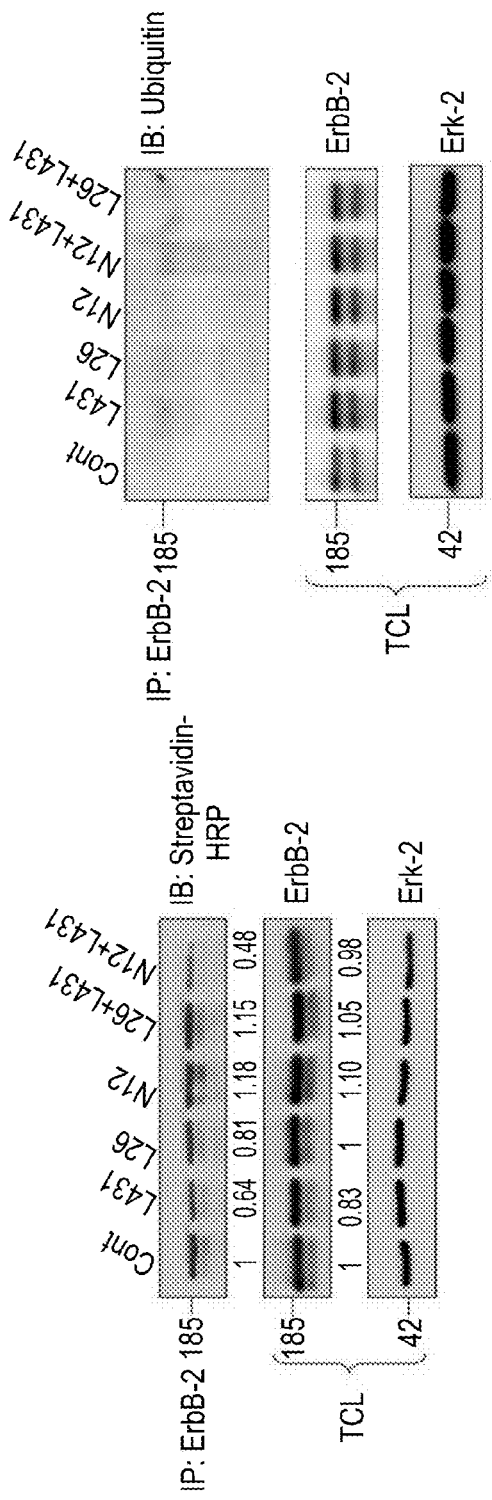
FIG. 5A
FIG. 5B
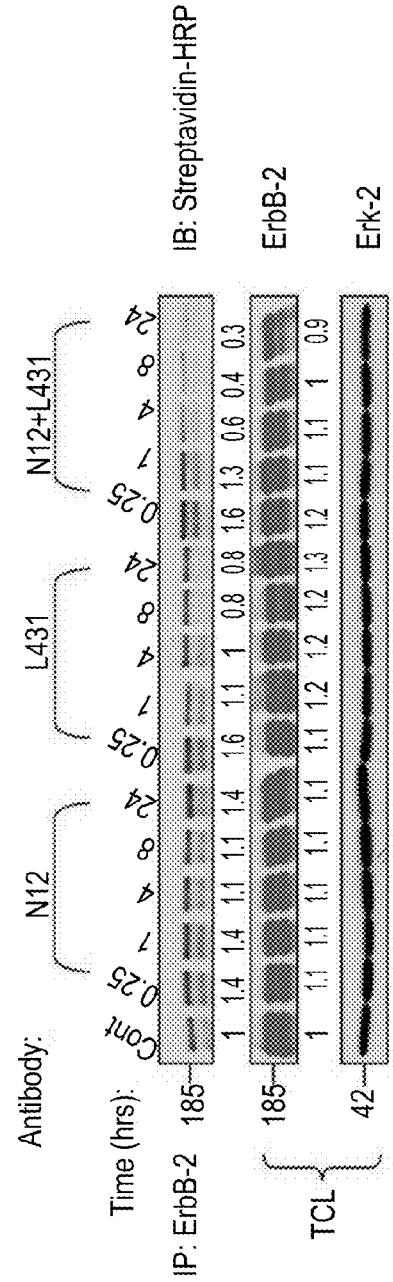
FIG. 5C

ANTIBODY COMBINATIONS AND USE OF SAME FOR TREATING CANCER

RELATED APPLICATIONS

This application is a division of U.S. patent application Ser. No. 13/063,940 filed on Mar. 15, 2011, which is a National Phase of PCT Patent Application No. PCT/IL2009/000816 having International Filing Date of Aug. 19, 2009, which claims the benefit of priority under 35 USC §119(e) of U.S. Provisional Patent Application No. 61/096,868 filed on Sep. 15, 2008. The contents of the above applications are all incorporated herein by reference.

STATEMENT REGARDING FEDERALLY SPONSORED RESEARCH OR DEVELOPMENT

This invention was made with government support under CA 072981 awarded by the NIH. The government has certain rights in the invention.

SEQUENCE LISTING STATEMENT

The ASCII file, entitled 60762SequenceListing.txt, created on Nov. 10, 2014, comprising 1,577 bytes, submitted concurrently with the filing of this application is incorporated herein by reference.

FIELD AND BACKGROUND OF THE INVENTION

The present invention, in some embodiments thereof, relates to antibody combinations and use of same in treating cancer.

ErbB-2/HER2 is a member of the epidermal growth factor receptor (EGFR) family. When trans-activated, ErbB-2/HER2 stimulates several downstream signaling cascades, including the mitogen-activated protein kinase cascade [reviewed in (1)]. This ligand-less receptor is moderately expressed in normal adult tissues, where it regulates cell growth and differentiation. By contrast, amplification of the corresponding gene and consequent overexpression of the HER2/ErbB-2 protein have been reported in 20-30% of tumors of the breast (2-4) and ovary (4). In general, erbB-2 gene amplification associates with enhanced metastatic potential and poor prognosis. Because ErbB-2 is expressed at relatively low levels in normal tissues, it makes an attractive target for immunotherapy. This was originally demonstrated in animals by Greene and colleagues (5), who targeted Neu, the rodent form of ErbB-2, and later developed into a widely used clinical strategy [reviewed in (6)]. Nevertheless, the molecular mechanisms underlying the growth inhibitory effects of anti-ErbB-2 monoclonal antibodies (mAbs) are not completely understood. Several mechanisms of action have been proposed, including immune mechanisms, such as antibody-dependent cellular cytotoxicity (ADCC) and complement-dependent cytototoxicity (CDC), increased cancer cell apoptosis and interference with signaling cascades [reviewed in (6)].

Clinical studies established that Trastuzumab (Herceptin®), a humanized mAb directed against ErbB-2, is active against ErbB-2-overexpressing metastatic breast cancer, leading to its approval for clinical use (7). The objective response rates to Trastuzumab monotherapy is relatively low (approximately 15%) and short lived (a median duration of 9 months) (8). On the other hand, mAbs seem to display a synergistic effect when combined with chemotherapy, probably due to interruption of ErbB-2-driven survival pathways (9). Still another strategy, relevant to pancreatic cancer, combines antibodies to EGFR and to ErbB-2 (10).

Yet another approach for improving the efficacy of antibody therapy refers to the use of mAb combinations. Indeed a number of studies have been effected using at least two antibody combinations directed at distinct epitopes of ErbB-2 [Drebin J. A. et al., Oncogene 2(3):273-277, 1988; Kasprzyk et al., Cancer Res. 52(10):2771-2776, 1992; Harwerth et al., Br. J. Cancer 68(6):1140-1145, 1993; Spiridon et al. Clin. Cancer Res. 8:1720-1730, 2002; Friedman et al. Proc. Natl. Acad. Sci. (2005) 102:1915-1920; and U.S. patent application Ser. No. 11/342,615]

SUMMARY OF THE INVENTION

According to an aspect of some embodiments of the present invention there is provided an article of manufacture comprising a packaging material identified for treating cancer packaging an anti-ErbB-2 antibody comprising the CDR sequences of CNCM I-4112 (N12) and an anti-ErbB-2 antibody comprising the CDR sequences of L431 deposit number CNCM I-4115.

According to an aspect of some embodiments of the present invention there is provided an article of manufacture comprising a packaging material identified for treating cancer packaging an anti-ErbB-2 antibody comprising the CDR sequences of deposit number CNCM I-4112 (N12) and an anti-ErbB-2 antibody comprising the CDR sequences of L26 deposit number CNCM I-4113.

According to an aspect of some embodiments of the present invention there is provided an article of manufacture comprising a packaging material identified for treating cancer packaging an anti-ErbB-2 antibody comprising the CDR sequences of N29 deposit number CNCM I-4114 and an anti-ErbB-2 antibody comprising the CDR sequences of L26 deposit number CNCM I-4113.

According to an aspect of some embodiments of the present invention there is provided an article of manufacture comprising a packaging material identified for treating cancer packaging an anti-ErbB-2 antibody comprising the CDR sequences of N29 deposit number CNCM I-4114 and an anti-ErbB-2 antibody comprising the CDR sequences of N12 deposit CNCM I-4112.

According to an aspect of some embodiments of the present invention there is provided an article of manufacture comprising a packaging material identified for treating cancer packaging an anti-ErbB-2 antibody comprising the CDR sequences of N29 deposit number CNCM I-4114 and an anti-ErbB-2 antibody comprising the CDR sequences of L431 deposit number CNCM I-4115.

According to an aspect of some embodiments of the present invention there is provided an article of manufacture comprising a packaging material identified for treating cancer packaging an anti-ErbB-2 antibody comprising the CDR sequences of the antibody selected from the group consisting of N12 (CNCM I-4112), L431 (CNCM I-4115), N29 (CNCM I-4114) and L26 (CNCM I-4113) and an additional anti-ErbB-2 antibody directed to a distinct epitope on ErbB-2, wherein when the anti-ErbB-2 antibody is L26 the anti-ErbB-2 antibody directed to the distinct epitope on ErbB-2 is not Trastuzumab.

According to an aspect of some embodiments of the present invention there is provided a method of treating cancer in a subject in need thereof, the method comprising administering to the subject an antibody combination selected from the group consisting of: an anti-ErbB-2 antibody comprising the CDR sequences of deposit number CNCM I-4112 (N12) and an anti-ErbB-2 antibody comprising the CDR sequences of L431 deposit number CNCM I-4115; an anti-ErbB-2 antibody comprising the CDR sequences of N12 deposit number CNCM I-4112 and an anti-ErbB-2 antibody comprising the CDR sequences of L26 deposit number CNCM I-4113; an anti-ErbB-2 antibody comprising the CDR sequences of N29 deposit number CNCM I-4114 and an anti-ErbB-2 antibody comprising the CDR sequences of L26 deposit number CNCM I-4113; an anti-ErbB-2 antibody comprising the CDR sequences of N29 deposit number CNCM I-4114 and an anti-ErbB-2 antibody comprising the CDR sequences of N12 deposit number CNCM I-4112; an anti-ErbB-2 antibody comprising the CDR sequences of N29 deposit number CNCM I-4114 and an anti-ErbB-2 antibody comprising the CDR sequences of L431 deposit number CNCM I-4115; an anti-ErbB-2 antibody comprising the CDR sequences of the antibody selected from the group consisting of N12 (CNCM I-4112), L431 (CNCM I-4115), N29 (CNCM I-4114) and L26 (CNCM I-4113) and an additional anti-ErbB-2 antibody directed to a distinct epitope on ErbB-2, wherein when the anti-ErbB-2 antibody is L26 the anti-ErbB-2 antibody directed to the distinct epitope on ErbB-2 is not trastuzumab.

According to an aspect of some embodiments of the present invention there is provided a method of identifying a combination of antibodies with a combined improved anti-tumor activity, the method comprising: (a) identifying binding epitopes of anti ErbB-2 antibodies; and (b) selecting a combination of at least two antibodies of the anti ErbB-2 antibodies exhibiting binding to different epitopes on the ErbB-2, at least one of the different epitopes being localized to a dimerization site of the ErbB-2, the combination of antibodies being with the combined improved anti-tumor activity.

According to some embodiments of the invention, the packaging material comprises at least two containers for separately packaging the antibodies.

According to some embodiments of the invention, the article of manufacture further comprising a chemotherapy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F are graphs showing in vivo anti-tumor effects of antibodies to ErbB-2/HER2 or combinations of same. Groups of seven CD-1/nude mice were injected subcutaneously with $5 \times 10^6$ N87 cells. mAbs (total: 720 µg per animal) were then injected intraperitoneally, either alone or in combinations, at days 7, 10 and 13 post grafting. Saline-injected mice were used for control (open circles). Combination treatments using the indicated antibodies are shown (closed circles), along with mAb1 alone (closed triangles) and mAb2 alone (open triangles). Tumors were measured once a week using calipers, and the mean tumor volume ($cm^3 \pm S.E.$) was plotted. Differences between the combined effects of N12+L431 or N12+L26 versus the individual mAbs are statistically significant (p<0.05).

FIGS. 2A-G are graphs showing in vitro growth inhibitory effects of antibodies to ErbB-2/HER2 and their combinations. Cultured N87 cells were treated for 72 h with increasing concentrations of the indicated antibodies (mAb1: closed triangles; mAb2: open triangles; HER indicates Herceptin®/Trastuzumab) or their combinations (closed circles). Thereafter, the MTT assay was performed and cell viability presented as percentage of control untreated cultures ($\pm S.D.$; n=8). Differences between the combined effects of N12+L431 (>0.1 µg/ml), N12+L26 (>0.1 µg/ml) and L26+Her (>0.6 µg/ml) versus the respective individual mAb are statistically significant (p<0.05).

FIGS. 3A-D are graphs illustrating antibody displacement analyses. The ability of unlabeled mAbs to displace the indicated cell surface-bound $^{125}$I-mAb was used as a measure of the degree of antigenic overlap. N87 cells were treated for 1 h at 4° C. with mAbs L431 (open circles), L26 (closed triangles), N29 (open triangles) and N12 (closed circles). The indicated radiolabeled mAbs (8 nM) were then added, and the cells were incubated for additional 15 min before determination of cell-bound radioactivity. The experiment was repeated thrice.

FIGS. 4A-B are autoradiograms showing the effects of mAbs and their combinations on the turnover rate of ErbB-2. N87 cells were incubated for 16 hrs with a mixture of [$^{35}$S] methionine and [$^{35}$S]cysteine and then chased for the indicated periods of time with non-radioactive medium containing 20 mg/ml (FIG. 4A) or the indicated lower concentrations (FIG. 4B) of anti-ErbB-2 mAbs. Residual $^{35}$S-labeled ErbB-2 was subjected to immunoprecipitation with a rabbit polyclonal antibody directed to the carboxyl terminus of the protein and electrophoretically separated. The numbers below lanes represent densitometric quantification of ErbB-2 relative to control, untreated cells.

FIGS. 5A-C are photographs showing the effects of antibody combinations on endocytosis and ubiquitinylation of ErbB-2, as evidenced by surface biotinylation. N87 cells were treated for either 8 h with the indicated mAbs (5 mg/ml; A), or they were treated with the indicated antibodies for increasing time intervals (B). Thereafter, bound antibodies were acid-stripped and the cell surface was biotinylated. Cells were then lysed, ErbB-2 immunoprecipitates (IP) or total cell lysates (TCL) immunoblotted (IB) using the indicated antibodies, or streptavidin horseradish peroxidase (HRP). Quantification of the signals is shown below the respective lanes. Ubiquitinylation of ErbB-2 (C) was determined by immunoblotting (with an anti-ubiquitin antibody from Babco/Covance) of ErbB-2 immunoprecipitates isolated from N87 cells treated with different mAbs for 1 h at 37° C.

DESCRIPTION OF EMBODIMENTS OF THE INVENTION

The present invention, in some embodiments thereof, relates to antibody combinations and use of same in treating cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the present invention to practice, the present inventors have uncovered through laborious experimentation and screening that mAbs directed at distinct epitopes of ErbB-2, especially epitopes involved in dimerization, are highly effective anti-tumor agents in vivo when used in combination. The superiority of these antibody combinations extends to the ability to inhibit tumor cell growth in vitro, which weakens involvement of immune mechanisms. Conversely, effective antibody combinations better than each antibody alone target surface ErbB-2 to intracellular degradation. These results suggest the use of antibody combinations uncovered by the present teachings in cancer immunotherapy especially for circumventing secondary drug resistance.

Thus, according to one aspect of the present invention there is provided a method of identifying a combination of antibodies with a combined improved anti-tumor activity.

The method according to this aspect of the present invention comprises: identifying binding epitopes of anti ErbB-2 antibodies; and selecting a combination of at least two antibodies of the anti ErbB-2 antibodies exhibiting binding to different epitopes on the ErbB-2 polypeptide, at least one of the different epitopes being localized to a dimerization site of the ErbB-2, the combination of antibodies being with the combined improved anti-tumor activity.

As used herein "a combination of antibodies" refers to at least two distinct antibodies, having different CDR sequences.

As used herein the phrase "anti tumor activity" refers to prevention of tumor formation and/or reduction of tumor size (e.g., volume) and/or metastasis potential.

As used herein the phrase "combined improved anti tumor activity" refers to at least additive but preferably synergistically improved anti tumor activity as explained hereinabove.

As used herein the term "synergy" refers a total affect that is greater than the sum of the individual contribution of each antibody.

As used herein "ErbB-2" refers to a receptor tyrosine kinase (RTK) of the epidermal growth factor receptor family, E.C. 2.7.10.1 also referred to as HER2, NEU and p185erbB-2.

Antibodies of this aspect of the present invention can be selected from pre-existing antibodies (e.g., publicly available hybridomas or recombinant antibody libraries, further described hereinbelow) or from newly generated antibodies produced according to methods which are well-known in the art and are further described hereinbelow.

Antibodies and methods of generating same are described at length in the following sections.

The term "antibody" as used in this invention includes intact molecules as well as functional fragments thereof, such as Fab, F(ab')2, and Fv. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

As mentioned the antibodies of the present invention bind different epitopes on ErbB-2, of which one is located at an ErbB-2 dimerization site (i.e., binding of the antibody thereto is sufficient for blocking ErbB-2 dimerization). The epitopes may be conformational or not and may be overlapping or not, provided that the two antibodies cannot displace each other when they bind ErbB-2.

Methods of identifying the binding epitopes of antibodies are well known in the art. Briefly, antibody binding epitopes can be determined by an antibody displacement assay. This may provide an initial understanding to the binding site. Antibody displacement techniques are well known in the art and described in length in the Examples section which follows. Thus for instance, if the antibody tested is displaced by an antibody which is known to bind to ErbB-2 dimerization domain then it is most likely that the antibody in question binds to at least a partly overlapping epitope.

At times a finer analysis is required, to this end epitope mapping techniques are employed. In this case the method of peptide scanning by Reineke et al. 1999 is typically employed (Curr. Top. Microbiol. Immunol. 243:23-36). The entire antigen sequence [e.g., extracellular portion of ErbB-2 or dimerization domain i.e., Residues 195-320 of ErbB-2/HER2 (ARCKGP (SEQ ID NO: 2), LPTDCCHEQC (SEQ ID NO: 3), AAGCTGPKHS (SEQ ID NO: 4), DCLACLHFNH (SEQ ID NO: 5), SGICELHCPA (SEQ ID NO: 6), LVTYNTDTFE (SEQ ID NO: 7), SMPNPEGRYT (SEQ ID NO: 8), FGASCVTACP (SEQ ID NO: 9), YNYLSTDVGS (SEQ ID NO: 10), CTLVCPLHNQ (SEQ ID NO: 11), EVTAEDGTQR (SEQ ID NO: 12), CEKCSKPCAR (SEQ ID NO: 13), VCYGLGMEHL (SEQ ID NO: 14),); See Insights into ErbB signaling from the structure of the ErbB2-pertuzumab complex. Franklin M C, et al, Cancer Cell 2004] is synthesized as linear 8 to 15 meric peptides that are subsequently tested for binding the antibody in question. The peptides may be synthesized using methods which are well known in the art (e.g., "SPOT" synthesis whereby the peptide is directly synthesized on a solid phase membrane e.g., cellulose). Solid-phase bound peptides are used for binding studies directly on the membrane (heterogeneous assay). Two different types of epitopes have to be considered: In linear (continuous) binding sites the key amino acids which mediate the contacts to the antibody are located within one part of the primary structure, usually not exceeding 15 amino acids in length. Peptides covering these sequences have affinities to the antibody which are within the range shown by the entire protein antigen. In discontinuous (conformational) binding sites the key residues are distributed over two or more binding regions which are separated in the primary structure. Upon folding, these binding regions are brought together on the protein surface to form a composite epitope. Substitutional analysis is typically effected to characterize epitopes which comprise amino acids which are buried in the antigen structure or when a side chain modification (e.g., glycosylation) is part of the epitope structure.

Once the binding properties of the antibodies are characterized, a combination of at least two antibodies of the anti ErbB-2 antibodies exhibiting binding to different epitopes on the ErbB-2 (as described hereinabove), is selected.

Those antibody combinations selected according to the present teachings can be further qualified having anti tumor activity using in vitro and in vivo methods which are well known in the art and described at length in the Examples section which follows.

While implementing the present teachings, the present inventors have successfully uncovered combinations of antibodies which are most effective in treating cancer in a subject in need thereof.

N12, L26, N29 and L431 have been deposited in the Collection Nationale de Cultures de Microorganismes INSTITUT PASTEUR 25, Rue du Docteur Roux F-75724 Paris CEDEX 15. Antibodies have been deposited under the Budapest Treaty. The materials have been registered on Jan. 13, 2009.

The registration numbers are as follows:

N12 CNCM I-4112;
L26 CNCM I-4113;
N29 CNCM I-4114;
L431 CNCM I-4115.

Thus the present invention, in some embodiments thereof, provides for an article of manufacture which comprises a packaging material identified, in print, for treating cancer. The packaging material comprises any combination of the following antibodies:

an anti-ErbB-2 antibody comprising the CDR sequences of N12 deposit number CNCM I-4112 and an anti-ErbB-2 antibody comprising the CDR sequences of L431 deposit number CNCM I-4115;

an anti-ErbB-2 antibody comprising the CDR sequences of N12 deposit number CNCM I-4112 and an anti-ErbB-2 antibody comprising the CDR sequences of L26 deposit number CNCM I-4113;

an anti-ErbB-2 antibody comprising the CDR sequences of N29 deposit number CNCM I-4114 and an anti-ErbB-2 antibody comprising the CDR sequences of L26 deposit number CNCM I-4113;

an anti-ErbB-2 antibody comprising the CDR sequences of N29 deposit number CNCM I-4114 and an anti-ErbB-2 antibody comprising the CDR sequences of N12 deposit number CNCM I-4112;

an anti-ErbB-2 antibody comprising the CDR sequences of N29 deposit number CNCM I-4114 and an anti-ErbB-2 antibody comprising the CDR sequences of L431 deposit number CNCM I-4115;

an anti-ErbB-2 antibody comprising the CDR sequences of the antibody selected from the group consisting of N12 (CNCM I-4112), L431 (CNCM I-4115), N29 (CNCM I-4114) and L26 (CNCM I-4113) and an additional anti-ErbB-2 antibody directed to a distinct epitope on ErbB-2, wherein when said anti-ErbB-2 antibody is L26 said anti-ErbB-2 antibody directed to a distinct epitope on ErbB-2 is not trastuzumab.

As used herein the term "subject" refers to a mammal, preferably a human subject.

As used herein the term "treating" refers to alleviating or diminishing a symptom associated with a disease (e.g., cancerous disease). Preferably, treating means cures, e.g., substantially eliminates, the symptoms associated with the disease.

As used herein the term "cancer" refers to a tumoral disease which depends on ErbB-2 (activity and/or expression) for onset and/or progression. Examples of cancer which can be treated in accordance with the present teachings include, but are not limited to, carcinoma, adenocarcinoma, lung cancer, liver cancer, colorectal cancer, brain, head and neck cancer (e.g., neuro/glioblastoma), breast cancer, ovarian cancer, transitional cell carcinoma of the bladder, prostate cancer, oral squamous cell carcinoma, bone sarcoma, biliary tract cancer such as gallbladder carcinoma (GBC), kidney cancer and pancreatic cancer.

Antibodies of the present invention can be administered to an organism per se, or in a pharmaceutical composition where they are mixed with suitable carriers or excipients (either individually or in a co-formulation).

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the antibodies accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Typically used models for analyzing the effect of the agents described herein on tumors are provided infra.

An animal model for ErbB-2 induced gallbladder carcinoma is described in Kawamoto et al. Cellular, Molecular, and Tumor Biology 89: Mouse Models of Prostate and Gastrointestinal Cancers Abstract Number 4313.

A mouse model for ErbB-2 dependent breast cancer is described in Liu et al. Cancer Research 65, 5325-5336, 2005.

Agus et al., "Response of Prostate Cancer to Anti-Her-2/neu Antibody in Androgen-dependent and -independent Human Xenograft Models" Cancer Research 59:4761-4764 (1999).

Kasprzyk et al., "Therapy of an Animal Model of Human Gastric Cancer Using a Combination of Anti-erbB-2 Monoclonal Antibodies" Cancer Research 52(10):2771-2776 (May 15, 1992).

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

It will be appreciated that the antibodies of the present invention can be provided to the individual with additional active agents to achieve an improved therapeutic effect as compared to treatment with the antibodies alone. In such therapy, measures (e.g., dosing and selection of the complementary agent) are taken to adverse side effects which may be associated with combination therapies.

Administration of such combination therapy can be simultaneous, such as in a single capsule having a fixed ration of these active agents, or in multiple capsules for each agent.

Thus, for example, the antibodies of the present invention can be administered along with analgesics, chemotherapeutic agents (e.g., anthracyclins), radiotherapeutic agents, hormonal therapy and other treatment regimens which are well known in the art.

It is expected that during the life of a patent maturing from this application many relevant antibodies will be developed and the scope of the term of the patent is intended to include all such new technologies a priori.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,853,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Procedures

Materials, Antibodies and Cells. Unless indicated, materials were purchased from Sigma (St. Louis, Mo.), cells from the American Type Culture Collection and antibodies from Santa Cruz Biotechnology (Santa Cruz, Calif.). "N87 cells" are NCI-N87 gastric carcinoma cells from the ATCC. Radiochemicals were purchased from Amersham (Buckinghamshire, UK). Trastuzumab was provided by Genentech (South San Francisco, Calif.). Generation of mAbs to ErbB-2 (i.e., N29, L431, N12 and L26) was previously described in Klapper L N, Vaisman N, Hurwitz E, Pinkas Kramarski R, Yarden Y, Sela M (1997) A subclass of tumor-inhibitory monoclonal antibodies to ErbB-2/HER2 blocks crosstalk with growth factor receptors. *Oncogene* 14: 2099-2109; and Stancovski I, Hurwitz E, Leitner O, Ullrich A, Yarden Y, Sela M (1991) Mechanistic aspects of the opposing effects of monoclonal antibodies to the ERBB2 receptor on tumor growth. *Proc Natl Acad Sci USA* 88: 8691-8695. The antibodies were purified on protein G Plus-Aagarose.

Surface Biotinylation Assay. Cells were incubated at 37° C. with mAbs and then transferred to ice and mAbs removed using a low pH solution (0.15 M acetic acid containing 0.15 M NaCl; 4 min). The cells were washed and incubated for 60 min at 4° C. with N-hydroxysuccinimide (NHS)-biotin (0.5 mg/ml; Calbiochem). Coupling of biotin was blocked with 15 mM glycine (15). Thereafter, cells were solubilized by the addition of lysis buffer [50 mM HEPES (pH 7.5), 150 mM NaCl, 10% glycerol, 1% Triton X-100, 1 mM EDTA, 1 mM EGTA, 1 mM phenylmethylsulfonyl fluoride, 50 mM sodium fluoride, 0.5 mM $Na_3VO_4$, 5 µg/ml leupeptin and 5 µg/ml aprotonin] and a rabbit antibody to ErbB-2 was used for immunoprecipitation.

Radiolabeling of Antibodies. MAbs (100 µg in 0.2 ml PBS) were radiolabeled using $Na^{125}I$ [5 µl; 0.5 mCi (18.5 MBq)] and chloramine-T (10 mg/10 µl). The reaction mixture was chromatographed on Sephadex G-25 yielding radiolabeled mAbs of 1-2 mCi/mg protein. MAb N29 was radiolabeled by using the [$^{125}I$]-Bolton-Hunter reagent (PerkinElmer Sciences, Inc; Boston, Mass.).

Antibody Competition Assay. N87 cells (250,000 cells/well) grown in 24-well plates were treated for 1 h at 4° C. with increasing concentrations of unlabeled mAbs. Radiolabelled mAbs (8 nM) were then added, and the cells incubated for additional 15 min at 4° C. After washing, the cells were solubilized in 0.5 N NaOH solution, prior to determination of radioactivity.

Inhibition of N87 Tumor Cell Growth in Culture. Antibodies were added to N87 cells (10,000 cells/well) grown in 96-well plates. Incubation at 37° C. proceeded for 72 h and cell viability determined by using the MTT [3-(4,5-dimethylthiazol-2-yl)-2,5-diphenyltetrazolium bromide] reagent (18).

Determination of the Effect of Antibodies on Receptor Turnover. N87 cells were labeled by incubation (16 h at 37° C.) in methionine- and cysteine-free medium supplemented with 10% dialyzed fetal calf serum and Promix, a mixture of [$^{35}S$]methionine and [$^{35}S$]cysteine (50 µCi/ml). Thereafter, cells were chased for various periods of time by incubation in fresh medium in the absence or presence of the antibodies. The cells were then washed, and lysates subjected to immunoprecipitation.

Tumorigenic Cell Growth in Animals. Female CD/nude mice were subcutaneously injected with N87 cells ($5 \times 10^6$/mouse). mAbs were injected intraperitoneally at days 7, 10 and 13 post grafting. Groups of 7 mice were used, and each mouse received 0.72 mg of purified mAb. Tumor parameters were measured once a week.

Statistical Analysis. Student's t-test (two-tailed) was used to test differences between the effects of antibody combinations and single treatment. Values of $p<0.05$ were considered statistically significant.

Example 1

Combinations of Monoclonal Anti-ErbB-2 Antibodies Collaboratively Inhibit Tumor Growth In Vivo To examine the effect of combining two antibodies, N87 cells were subcutaneously injected into athymic mice, which elicited rapidly growing tumors. Thereafter, the four mAbs or their six combinations were intraperitoneally injected into groups of seven mice. FIGS. 1a-f depict the average tumor volume of each group as a function of post-grafting time. While the antibodies differed in their therapeutic efficacy, with only one exception (a combination of mAbs L431 and L26, FIG. 1d), antibody combinations more effectively inhibited tumor growth than each antibody alone. Notably, tumors were completely eradicated in at least four of seven mice after treatment with the two most effective combinations, namely: L26 plus N12 and L431 plus N12. Moreover, this effect persisted six weeks after the last injection. Interestingly, when singly applied, N29 was not effective. Nevertheless, this mAb enhanced the inhibitory effect of other mAbs, but tumors initially inhibited by N29-containing combinations displayed re-growth (FIGS. 1a-b, f). In conclusion, the majority of antibody combinations tested showed clear synergistic anti-tumor effects.

Example 2

Antibody Combinations Inhibit Cell Growth In Vitro

The synergistic in vivo effects observed may be due to immunological mechanisms (e.g., ADCC). Hence, it is expected that antibody synergy would not extend to an in vitro test, such as the MTT cell proliferation assay. FIGS. 2a-g depict the results of an assay performed with N87 cells incubated for 72 h with various antibodies and their combinations. Remarkably, strong correlation was found with most antibody combinations between the results obtained in this assay and the in vivo experiments (FIGS. 1a-f): four of the six combinations exhibited synergistic effects. Moreover, the relative potency of the various combinations was preserved in vitro. For instance, the superior antibody combination in animals, namely N12+L431, was also the most potent in vitro combination, yielding 54% reduction in cell proliferation already at 0.3 μg/ml. Likewise, our least potent in vivo combination, namely L26+L431, displayed no synergy in vitro. Notably, the N29 antibody elicited no inhibitory effects both in vitro and in animals, and when tested in combinations it did not improve the effects of mAbs N12 and L431. Yet, this antibody reproducibly enhanced the in vitro anti-proliferative effect of L26 (FIG. 2f), which attributes a role for antigen cross-linking by a second antibody.

We previously reported that a combination of L26, an antibody capable of inhibiting heterodimerization of ErbB-2 (16), and Trastuzumab displays synergy in an in vivo anti-tumor test (15). Extension of this analysis is shown in FIG. 2g: the combination is significantly more potent than each antibody alone. To exclude complement involvement, the MTT assay was repeated using a serum replacement mixture containing heat-treated albumin Because the synergistic effects of antibody combinations were observed also in the absence of serum (data not shown), it is concluded that neither CDC nor ADCC contribute to the ability of anti-ErbB-2 antibodies to collaborate in vitro. Taken together, the overall similarity between the in vivo and in vitro effects of antibody combinations implies that the synergistic anti-growth effects are mediated by activities intrinsic to the antibody molecules.

Example 3

Characterization of Epitope Sharing by Anti-ErbB-2 Antibodies

Previous analysis of a panel of antibodies to EGFR indicated that mAb synergy requires interactions with two mutually distinct antigenic determinants (15). Therefore, the ability of each anti-ErbB-2 mAb to displace radiolabeled versions of the other mAbs, was analyzed. The results shown in FIG. 3 confirmed that the non-synergizing pair of antibodies, namely L26 and L431, is cross-competitive. On the other hand, pairs of mAbs that displayed synergy both in vivo and in vitro, including L431 plus N12 and L26 plus N12, bind distinct epitopes of ErbB-2. In the case of N29, the unlabeled antibody did not interfere with the binding of any of the radiolabeled antibodies, while the binding of a radiolabeled derivative of N29 was reduced by L431, possibly through steric interference. Consistent with this possibility, an attempt to map the N29 epitope has failed, suggesting that N29 recognizes a carbohydrate-containing epitope (19).

Example 4

Specific Antibody Combinations Accelerate Removal of ErbB-2 from the Cell Surface The interaction of receptor tyrosine kinases with their respective ligands is often coupled to rapid endocytosis and receptor degradation in lysosomes. It was shown that mAbs can induce an analogous, albeit slower effect (20), which is associated with inhibition of tumorigenesis (12). Therefore, the potential of the present sets of mAbs to alter the turnover rate of ErbB-2 was tested. To this end, N87 cells were biosynthetically labeled and then chased in fresh, mAb-containing medium. As shown in FIG. 4A, among the four mAbs tested, L431 remarkably accelerated degradation of ErbB-2, and this was slightly enhanced by the addition of N12. Because the non-synergistic L26+L431 combination was less effective, various concentrations of each antibody were tested, as well as the two combinations (FIG. 4B; chase of 2 h). The results confirmed that the L431+N12 combination is superior at a relatively low antibody concentration, but this difference became less apparent at higher concentrations.

Because pulse-chase analysis examines the overall pool of ErbB-2, but mAbs interact with only the surface-exposed receptors, surface biotinylation was applied. Cells were surface-labeled with biotin following incubation for 8 hours with single mAbs, or their combinations. Thereafter, antibodies were acid-stripped and ErbB-2 immunoprecipitated. As depicted in FIG. 5A, the combination of mAbs L431 and N12 most potently down-regulated ErbB-2 from the cell surface. Interestingly, the other combination, L431+L26, was less effective than L431 alone, in line with their competitive interactions (FIGS. 3a-d). The superiority of the L431+N12 combination is evident also from the time course of ErbB-2 down-regulation (FIG. 5B): almost all surface ErbB-2 molecules were cleared from the cell surface following a 24-h long incubation with the L431+N12 combination, but each antibody exerted only a limited effect.

Sorting of receptor tyrosine kinases (e.g., EGFR) for intracellular degradation involves their ubiquitinylation, which recruits to the internalizing receptor ubiquitin-binding coat adaptors, such as Epsin [reviewed in (21)]. It was proposed that this mechanism may underlie mAb-induced degradation of ErbB-2 (22). Hence, by employing anti-ubiquitin antibodies the ability of mAbs and their combinations to enhance ErbB-2 ubiquitinylation was addressed. This assay revealed weak, but reproducible mAb-induced ubiquitinylation of ErbB-2. Interestingly, L431 displayed higher effects than other mAbs, especially when combined with the non-competitive N12 mAb. Once again, when combined with the competitive L26 antibody, the ubiquitinylation effect of L431 decreased. In conclusion, certain mAbs enhance ubiquitinylation of ErbB-2 and effectively target the surface-localized sub-population of this receptor to intracellular degradation. Combining two non-competitive mAbs enhances this activity, which correlates with the synergistic growth inhibitory effects of such combinations (FIGS. 1a-f and 2a-g)

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

1. Citri A, Yarden Y (2006) EGF-ERBB signalling: towards the systems level. *Nat Rev Mol Cell Biol* 7: 505-16.
2. King C R, Swain S M, Porter L, Steinberg S M, Lippman M E, Gelmann E P (1989) Heterogeneous expression of erbB-2 messenger RNA in human breast cancer. *Cancer Res* 49: 4185-91.
3. Slamon D J, Clark G M, Wong S G, Levin W J, Ullrich A, McGuire W L (1987) Human breast cancer: correlation of relapse and survival with amplification of the HER-2/neu oncogene. *Science* 235: 177-82.
4. Slamon D J, Godolphin W, Jones L A, Holt J A, Wong S G, Keith D E, Levin W J, Stuart S G, Udove J, Ullrich A, et al. (1989) Studies of the HER-2/neu proto-oncogene in human breast and ovarian cancer. *Science* 244: 707-12.
5. Drebin J A, Link V C, Weinberg R A, Greene M I (1986) Inhibition of tumor growth by a monoclonal antibody reactive with an oncogene-encoded tumor antigen. *Proc Natl Acad Sci USA* 83: 9129-33.
6. Ben-Kasus T, Schechter B, Sela M, Yarden Y (2007) Cancer therapeutic antibodies come of age: Targeting minimal residual disease. *Mol. Oncology* 1: 42-54.
7. Carter P, Presta L, Gorman C M, Ridgway J B, Henner D, Wong W L, Rowland A M, Kotts C, Carver M E, Shepard H M (1992) Humanization of an anti-p185HER2 antibody for human cancer therapy. *Proc Natl Acad Sci USA* 89: 4285-9.
8. Cobleigh M A, Vogel C L, Tripathy D, Robert N J, Scholl S, Fehrenbacher L, Wolter J M, Paton V, Shak S, Lieberman G, Slamon D J (1999) Multinational study of the efficacy and safety of humanized anti-HER2 monoclonal antibody in women who have HER2-overexpressing metastatic breast cancer that has progressed after chemotherapy for metastatic disease. *J Clin Oncol* 17: 2639-48.
9. Arteaga C L, Winnier A R, Poirier M C, Lopez Larraza D M, Shawver L K, Hurd S D, Stewart S J (1994) p185c-erbB-2 signal enhances cisplatin-induced cytotoxicity in human breast carcinoma cells: association between an oncogenic receptor tyrosine kinase and drug-induced DNA repair. *Cancer Res* 54: 3758-65.
10. Larbouret C, Robert B, Navarro-Teulon I, Thezenas S, Ladjemi M Z, Morisseau S, Campigna E, Bibeau F, Mach J P, Pelegrin A, Azria D (2007) In vivo therapeutic synergism of anti-epidermal growth factor receptor and anti-HER2 monoclonal antibodies against pancreatic carcinomas. *Clin Cancer Res* 13: 3356-62.
11. Drebin J A, Link V C, Greene M I (1988) Monoclonal antibodies specific for the neu oncogene product directly mediate anti-tumor effects in vivo. *Oncogene* 2: 387-94.
12. Kasprzyk P G, Song S U, Di Fiore P P, King C R (1992) Therapy of an animal model of human gastric cancer using a combination of anti-erbB-2 monoclonal antibodies. *Cancer Res* 52: 2771-2776.
13. Nahta R, Hung M C, Esteva F J (2004) The HER-2-targeting antibodies trastuzumab and pertuzumab synergistically inhibit the survival of breast cancer cells. *Cancer Res* 64: 2343-6.
14. Spiridon C I, Ghetie M A, Uhr J, Marches R, Li J L, Shen G L, Vitetta E S (2002) Targeting multiple Her-2 epitopes with monoclonal antibodies results in improved antigrowth activity of a human breast cancer cell line in vitro and in vivo. *Clin Cancer Res* 8: 1720-1730.
15. Friedman L M, Rinon A, Schechter B, Lyass L, Lavi S, Bacus S S, Sela M, Yarden Y (2005) Synergistic downregulation of receptor tyrosine kinases by combinations of mAbs: Implications for cancer immunotherapy. *Proc. Natl. Acad. Sci. U.S.A.* 102: 1915-20.
16. Klapper L N, Vaisman N, Hurwitz E, Pinkas Kramarski R, Yarden Y, Sela M (1997) A subclass of tumor-inhibitory monoclonal antibodies to ErbB-2/HER2 blocks crosstalk with growth factor receptors. *Oncogene* 14: 2099-2109.
17. Stancovski I, Hurwitz E, Leitner O, Ullrich A, Yarden Y, Sela M (1991) Mechanistic aspects of the opposing effects of monoclonal antibodies to the ERBB2 receptor on tumor growth. *Proc Nall Acad Sci USA* 88: 8691-8695.
18. Mosmann T (1983) Rapid colorimetric assay for cellular growth and survival: application to proliferation and cytotoxicity assays. *J Immunol Methods* 65: 55-63.
19. Yip Y L, Smith G, Koch J, Dubel S, Ward R L (2001) Identification of epitope regions recognized by tumor inhibitory and stimulatory anti-ErbB-2 monoclonal antibodies: implications for vaccine design. *J Immunol* 166: 5271-8.
20. Yarden Y (1990) Agonistic antibodies stimulate the kinase encoded by the neu protooncogene in living cells but the oncogenic mutant is constitutively active. *Proc. Natl. Acad. Sci. USA* 87: 2569-2573.
21. Marmor M D, Yarden Y (2004) Role of protein ubiquitylation in regulating endocytosis of receptor tyrosine kinases. *Oncogene* 23: 2057-2070.
22. Klapper L N, Waterman H, Sela M, Yarden Y (2000) Tumor-inhibitory antibodies to HER-2/ErbB-2 may act by recruiting c-Cbl and enhancing ubiquitination of HER-2. *Cancer Res.* 60: 3384-3388.
23. Clynes R A, Towers T L, Presta L G, Ravetch J V (2000) Inhibitory Fc receptors modulate in vivo cytoxicity against tumor targets. *Nat. Med.* 6: 443-446.
24. Spiridon C I, Guinn S, Vitetta E S (2004) A comparison of the in vitro and in vivo activities of IgG and F(ab')2 fragments of a mixture of three monoclonal anti-Her-2 antibodies. *Clin. Cancer Res.* 10: 3542-51.
25. Fan Z, Lu Y, Wu X, Mendelsohn J (1994) Antibody-induced epidermal growth factor receptor dimerization mediates inhibition of autocrine proliferation of A431 squamous carcinoma cells. *J. Biol. Chem.* 269: 27595-27602.
26. Hurwitz E, Klapper L N, Wilchek M, Yarden Y, Sela M (2000) Inhibition of tumor growth by poly(ethylene glycol) derivatives of anti-ErbB2 antibodies. *Cancer Immunol Immunother* 49: 226-34.
27. Xu F, Lupu R, Rodriguez G C, Whitaker R S, Boente M P, Berchuck A, Yu Y, DeSombre K A, Boyer C M, Bast R C, Jr. (1993) Antibody-induced growth inhibition is mediated through immunochemically and functionally distinct epitopes on the extracellular domain of the c-erbB-2 (HER-2/neu) gene product p185. *Int. J. Cancer* 53: 401-408.

28. Garrett T P, McKern N M, Lou M, Elleman T C, Adams T E, Lovrecz G O, Kofler M, Jorissen R N, Nice E C, Burgess A W, Ward C W (2003) The crystal structure of a truncated ErbB2 ectodomain reveals an active conformation, poised to interact with other ErbB receptors. *Mol Cell* 11: 495-505.
29. Agus D B, Akita R W, Fox W D, Lewis G D, Higgins B, Pisacane P I, Lofgren J A, Tindell C, Evans D P, Maiese K, Scher H I, Sliwkowski M X (2002) Targeting ligand-activated ErbB2 signaling inhibits breast and prostate tumor growth. *Cancer Cell* 2: 127-37.
30. Baselga J, Cameron D, Miles D, Verma S, Climent M, Ross G, Gimenez V, Gelmon K (2007) Objective response rate in a phase II multicenter trial of pertuzumab (P), a HER2 dimerization inhibiting monoclonal antibody, in combination with trastuzumab (T) in patients (pts) with HER2-positive metastatic breast cancer (MBC) which has progressed during treatment with T. *Journal of Clinical Oncology* (2007 *ASCO Annual Meeting Proceedings Part I*) 25: Abstract No. 1004.
31. Baulida J, Kraus M H, Alimandi M, Di Fiore P P, Carpenter G (1996) All ErbB receptors other than the epidermal growth factor receptor are endocytosis impaired. *J. Biol. Chem.* 271: 5251-5257.
32. Pinkas-Kramarski R, Soussan L, Waterman H, Levkowitz G, Alroy I, Klapper L, Lavi S, Seger R, Ratzkin B J, Sela M, Yarden Y (1996) Diversification of Neu differentiation factor and epidermal growth factor signaling by combinatorial receptor interactions. *Embo J.* 15: 2452-2467.
33. Worthylake R, Opresko L K, Wiley H S (1999) ErbB-2 amplification inhibits down-regulation and induces constitutive activation of both ErbB-2 and epidermal growth factor receptors. *J. Biol. Chem.* 274: 8865-8874.
34. Katzmann D J, Odorizzi G, Emr S D (2002) Receptor downregulation and multivesicular-body sorting. *Nat Rev Mol Cell Biol* 3: 893-905.
35. Diestel S, Schaefer D, Cremer H, Schmitz B (2007) NCAM is ubiquitylated, endocytosed and recycled in neurons. *J Cell Sci* 120: 4035-49.
36. Hynes N E, Lane H A (2005) ERBB receptors and cancer: the complexity of targeted inhibitors. *Nat Rev Cancer* 5: 341-54.

What is claimed is:

1. A method of treating pancreatic cancer in a subject in need thereof, the method comprising administering to the subject an anti-ErbB-2 antibody comprising the CDR sequences of the N12 antibody under deposit number CNCM I-4112 and adminstering to the subject an anti-ErbB-2 antibody comprising the CDR sequences of the L26 antibody under deposit number CNCM I-4113; wherein said administration of said antibodies has improved anti-pancreatic tumor activity in-vivo compared to administration of either antibody alone.

2. The method of claim 1, wherein said administering comprises intravenous administration.

3. The method of claim 1, wherein said anti-ErbB-2 antibodies are in a co-formulation.

4. The method of claim 1, wherein said anti-ErbB-2 antibodies are in separate formulations.

5. The method of claim 1, wherein said subject is a human subject.

* * * * *

SEQUENCE LISTING

```
<160> NUMBER OF SEQ ID NOS: 1

<210> SEQ ID NO 1
<211> LENGTH: 126
<212> TYPE: PRT
<213> ORGANISM: Homo sapiens
<220> FEATURE:
<221> NAME/KEY: misc_feature
<223> OTHER INFORMATION: Residues 195-320 of ErbB-2/HER2

<400> SEQUENCE: 1

Ala Arg Cys Lys Gly Pro Leu Pro Thr Asp Cys Cys His Glu Gln Cys
1               5                   10                  15

Ala Ala Gly Cys Thr Gly Pro Lys His Ser Asp Cys Leu Ala Cys Leu
            20                  25                  30

His Phe Asn His Ser Gly Ile Cys Glu Leu His Cys Pro Ala Leu Val
        35                  40                  45

Thr Tyr Asn Thr Asp Thr Phe Glu Ser Met Pro Asn Pro Glu Gly Arg
    50                  55                  60

Tyr Thr Phe Gly Ala Ser Cys Val Thr Ala Cys Pro Tyr Asn Tyr Leu
65                  70                  75                  80

Ser Thr Asp Val Gly Ser Cys Thr Leu Val Cys Pro Leu His Asn Gln
                85                  90                  95

Glu Val Thr Ala Glu Asp Gly Thr Gln Arg Cys Glu Lys Cys Ser Lys
            100                 105                 110

Pro Cys Ala Arg Val Cys Tyr Gly Leu Gly Met Glu His Leu
        115                 120                 125
```